(12) United States Patent
Göbel et al.

(10) Patent No.: US 9,186,233 B2
(45) Date of Patent: Nov. 17, 2015

(54) CLOSING SYSTEM FOR A NATURAL OR ARTIFICIAL ANUS

(76) Inventors: Lothar Göbel, Würzburg (DE); Fred Göbel, Wilhelmsfeld (DE)

(*) Notice: Subject to any disclaimer, the term of this patent is extended or adjusted under 35 U.S.C. 154(b) by 1031 days.

(21) Appl. No.: 12/931,907

(22) Filed: Feb. 14, 2011

(65) Prior Publication Data
US 2011/0306823 A1 Dec. 15, 2011

Related U.S. Application Data

(63) Continuation-in-part of application No. 10/565,316, filed as application No. PCT/EP2004/008256 on Jul. 23, 2004, now abandoned.

(30) Foreign Application Priority Data

Jul. 23, 2003 (DE) .................. 103 33 706

(51) Int. Cl.
*A61M 5/178* (2006.01)
*A61F 2/00* (2006.01)
*A61F 5/445* (2006.01)

(52) U.S. Cl.
CPC ............... *A61F 2/0013* (2013.01); *A61F 5/445* (2013.01)

(58) Field of Classification Search
CPC .................. A61F 2/0013; A61F 5/445; A61F 2005/4455; A61F 2025/1052; A61F 2025/1065; A61F 2210/1067; A61F 25/1002; A61F 25/1018; A61F 25/1027
USPC ...................................................... 604/164.01
See application file for complete search history.

(56) References Cited

U.S. PATENT DOCUMENTS

| | | | |
|---|---|---|---|
| 2,324,520 A | 7/1943 | Lamson | |
| 3,802,418 A | 4/1974 | Clayton | |
| 3,828,782 A | 8/1974 | Polin | |
| 4,850,953 A | 7/1989 | Haber et al. | |
| 5,545,179 A * | 8/1996 | Williamson, IV | 606/213 |
| 5,569,216 A | 10/1996 | Kim | |
| 5,667,479 A * | 9/1997 | Kieturakis | 600/207 |
| 6,527,755 B1 | 3/2003 | Salama | |
| 2003/0181879 A1 | 9/2003 | Mulhauser et al. | |

* cited by examiner

*Primary Examiner* — Jason Flick
(74) *Attorney, Agent, or Firm* — Pandiscio & Pandiscio

(57) ABSTRACT

The invention relates to a closing system for a natural or an artificial anus, the system comprising an inflatable balloon having a generally toroidal structure, and composed of a plane tubular section folded in on itself, the ends of which extend coaxially within each other and are linked to a sleeve.

32 Claims, 14 Drawing Sheets

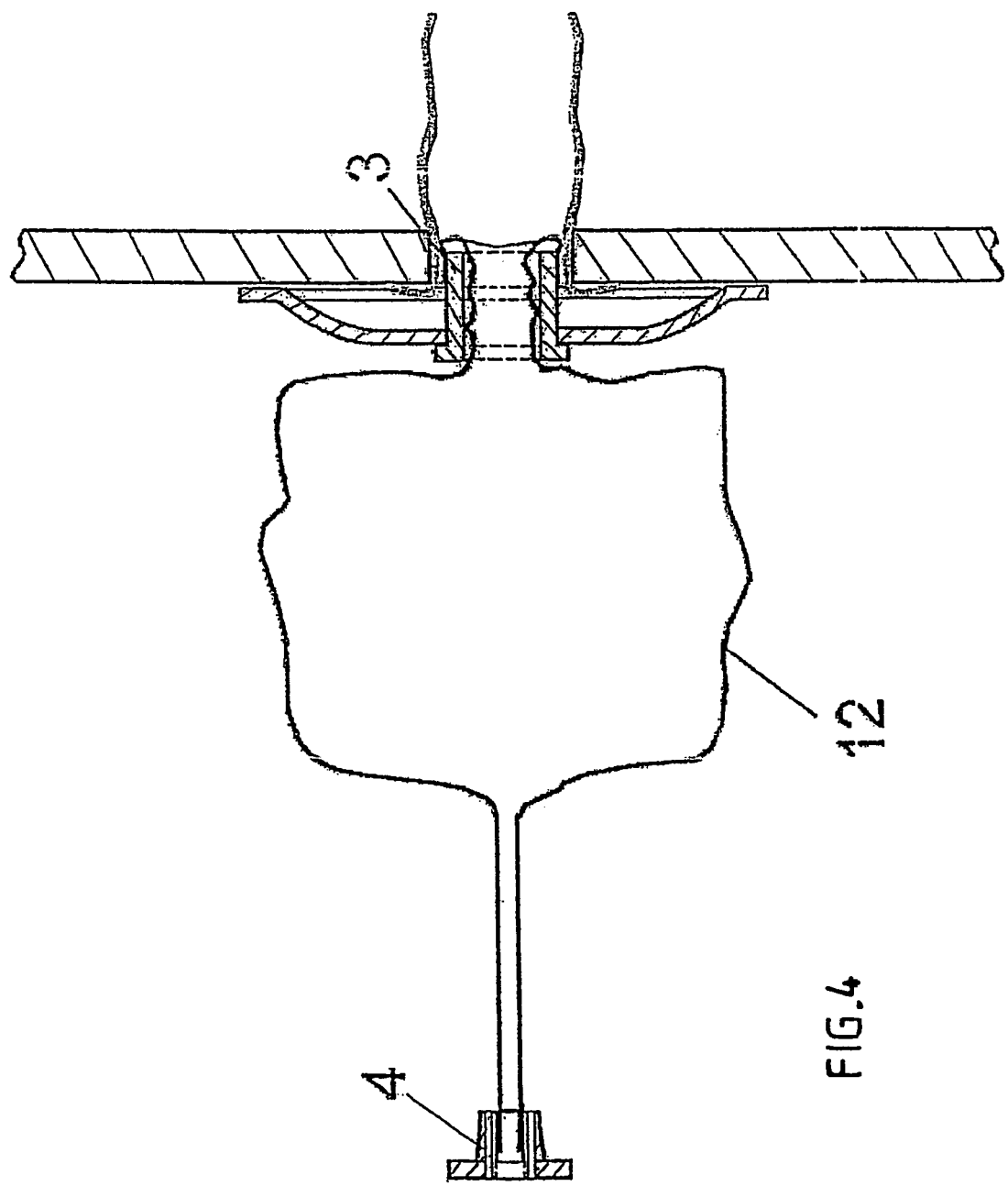

CLOSING SYSTEM FOR A NATURAL OR ARTIFICIAL ANUS

CROSS-REFERENCE TO RELATED APPLICATION

This application is a continuation-in-part of U.S. patent application Ser. No. 10/565,316, filed Jul. 13, 2006, in the name of Lothar Göbel.

BACKGROUND OF THE INVENTION

1. Field of the Invention

The invention is directed to a closing system for a natural or an artificial intestinal outlet, the system including an inflatable balloon having an approximately toroidal structure.

2. Description of the Prior Art

The medical management of intestinal stomata continues to be an ongoing, daily problem. One very common method is to collect stool in receptacles that are used in the form of adhesive bags. This extracorporeal storage is associated with the problem of odor nuisance, and above all the risk of loosening of the bag from the skin and soiling.

In addition to extracorporeal collection systems, seals were developed with the objective to create an indwelling seal of the stoma, allowing intermittent emptying of the stool when removing the sealing structure from the body. Fundamental problems of such closure systems proved to be the traumatic effect of the sealing device on the exposed anatomical structures during prolonged placement, as well as the insufficient anchoring of the sealing system inside the body, and tendency to slip out of the stoma when, e.g., the intra-abdominal pressure abruptly increases.

For the treatment of fecal incontinence, similar approaches have been taken. In the care of immobilized patients, bag like collecting systems are established, which are affixed to the peri-anal skin. The bag usually has a tube element connected to it, draining the stool from the bag-like collector to a remote collecting unit. Problematic remain the effect of the bag fixation on the body skin and the degradation of the peri-anal skin, due to its permanent exposure to the stool. Not to mention the tendency of the affixed bag to loosen and to soil the care area.

Alternatively to peri-anally affixed bags, stool draining catheters, so called rectal tubes, can be used. A large bore catheter element is inserted through the anus into the rectum, taking up the feces there and draining them into a connected receptacle. Because of their limited flexibility, rectal tubes can have severe traumatic effects on the exposed colo-rectal and anal structures, reaching from ulceration of the surface to penetration of the organ wall.

Mobile patients, suffering from fecal incontinence, are, in few cases, using closure plug like devices, introduced transanally into the rectum, enabling a certain retention and seal effect. These so called rectal plugs are known for a tendency to slip out of the rectum, as well as painful ano-rectal irritations, when being removed by the patient.

The disadvantages of the described prior art give rise to the problem initiating the invention, that of creating a closing system for a natural or artificial intestinal outlet, that is of uncomplicated construction and manufactured from inexpensive materials, can readily be inserted into the body, has sufficient anchoring properties, follows organ and body movements, and causes the smallest possible pressure load on the exposed tissues, enabling indwelling placement with the least possible tissue irritation and risk of tissue perfusion impairment. Further, the invented device introduces a technique of allowing for a seal against solid and semisolid bowel contents, but at the same time granting the continuous release of bowel gas from the intestine to the outside of the body, thereby preventing the progressive flatulence of the abdomen. Beyond, the invented device further grants an access channel for the infusion of an irrigation fluid, enabling the patient to install the fluid and move freely, until the peristaltic bowel activity sets in and the seal is being removed.

SUMMARY OF THE INVENTION

The solution to this problem is achieved by means of an inflatable balloon, having an approximately toroidal structure, formed of a hose segment with a two-dimensional surface, which is inverted to itself, whereby its two ends extend roughly coaxially inside each other and are connected to a sleeve element, or are each connected to a respective sleeve.

The balloon structure is fabricated to its full working state dimension during the manufacturing process and it is made from a thin-walled, soft foil material of low compliance, preferably of a polymer with a compliance like polyvinyl chloride or lower, especially of a polymer with a compliance like polyethylene or lower, granting sufficient stability of the preshaped geometry, when the filling pressure inside the balloon structure increases.

In this context, the compliance of a material $C_{mat.}$, especially of a polymer, is meant as the reciprocal Young's modulus (modulus of elasticity) E of this material:

$$C_{mat.}=1/E$$

The higher the compliance the more elastic the material, therefore steel (E=200 GPa) has a lower compliance than rubber (E=0.01 ... 0.1 GPa).

Vulcanization of natural rubber occurs when elements such as sulfur are introduced to the media. In industry, sulfur or similar additions are titrated to the desired compliance performance definition of the media. On the other hand, the compliance preferred by the present invention is lower than that of rubber, so vulcanization is not conducted at such substances. According to the present invention, the material of the balloon neither contains a silicone elastomer nor a rubber.

The balloon according to the present invention is made from a material with "low compliance". In the context of this patent application, this expression shall comprise especially the following materials: Polyethylene (PE), especially low-density polyethylene, polyethylene terephthalate (PET), ethylene vinyl acetate (EVA), polyvinyl chloride (PVC), PVC/EVA blends, as well as polyurethane (PUR), especially with a Shore hardness $S_A$ of 80 A or more, or with a Shore hardness $S_D$ of 30 D or more, for example $S_D$ of 40 D or more, preferably $S_D$ of 50 D or more, especially $S_D$ of 60 D or more, like, e.g., Pellethane 2363 from Dow Chemical or, e.g., comparable polymers from the Elastollan LP 9291 family from BASF.

According to the measuring principle of the Shore hardness, where a ball or an apex is pressed elastically into a test specimen, the Young's modulus and the Shore hardness are somehow correlated, and the Young's modulus seems to be an exponential function of the Shore hardness, especially $$\log E = 0.0235\ S - 0.6403,$$

or $$E = \exp(0.0235\ S - 0.6403),$$

whereby
E is the Young's modulus in MPa, and
S can be:

$$S=S_A \text{ for } 20<S_A<80, \text{ or}$$

$$S=S_D+50 \text{ for } 30<S_D<85.$$

So, the Young's modulus, and the material compliance can be estimated by the Shore hardness $S_A$ or $S_D$ of a material.

For example, the Young's moduli of some preferred materials are as follows:

For polyethylene, E=0.2 GPa, for polyvinyl chloride, E=1 ... 3 GPa, for polyethylene terephthalate, E=1 ... 5 GPa. As these values are clearly above the Young's modulus of for example rubber, where E=0.01 ... 0.1 GPa, the compliance $C_{mat}$ of such materials is rather low.

For understanding the behaviour of a container, especially a balloon, made from such material, the following relationships are to be considered:

A balloon filled with a medium like air, changes its size because of a pressure gradient across the wall of the balloon, the so-called transmural pressure $P_{transmural}$, which is the difference of the pressure $P_{in}$ inside the balloon minus the pressure $P_{out}$ outside the balloon:

$$P_{transmural} = P_{in} - P_{out}.$$

A positive transmural pressure ($P_{in} > P_{out}$) works to expand the balloon.

But the transmural pressure is not the only factor determining the expansion or contraction of a balloon. In some cases, the container itself has innate properties that give it a tendency to collapse or expand. This tendency towards collapse or expansion is called elastic recoil pressure $P_{el}$.

The actual behaviour of a balloon (collapse or expansion) is the result of both the transmural pressure and the elastic recoil pressure:

$$P_{expansion\ or\ contraction} = P_{transmural} + P_{el}.$$

If the balloon is in a static condition and does not expand or contract, the resultant pressure $P_{expansion\ or\ contraction}$ is zero, and both components have equal values but different algebraic signs:

$$P_{transmural} = -P_{el}.$$

If—like at the present invention—the balloon structure is fabricated to its full working state dimension, it can expand to this working state dimension without any elastic recoil pressure:

$$P_{el} = 0.$$

Then $$P_{transmural} = 0,$$

$$P_{in} = P_{out}.$$

This means that the pressure inside the balloon is the same as the pressure outside of it.

If $P_{out}$=const., then $P_{in}$=const., too. Therefore, upon filling such a balloon up to its working dimension, $\Delta P=0$, while $\Delta V = V_{preshaped} \neq 0$.

On the other hand, it is plausible that the size or volume V of a balloon made from an elastic material, for example from a silicone elastomer, is a function of the pressure inside or the transmural pressure:

$$V_{balloon} = V_{balloon}(P_{transmural})$$

Elastance is a measure of the tendency of a structure to return to its original form after removal of a deforming force; it is the reciprocal of its compliance C.

The compliance C of a balloon made from an elastic material is calculated using the following equation, where $\Delta V_{balloon}$ is the change in volume of the balloon, and $\Delta P$ is the change in transmural pressure:

$$C = \Delta V_{balloon} / \Delta P_{transmural}$$

This is the slope of the function $V_{balloon}(P_{transmural})$. Such slope is finite for a not preformed balloon made of an elastic material, but is infinite for a preformed balloon fabricated from a material with low compliance, which is filled up to its preshaped working volume.

This is a serious distinction between a balloon which is not fabricated to its full working state dimension during the manufacturing process, but made from an elastic material so that it may expand under pressure, and a balloon preshaped to its full working state dimension. Another rather serious distinction is that in the first case, the transmural pressure is positive:

$$P_{in} > P_{out},$$

which means that the balloon is swollen and bulging, whereas in the latter case, the transmural pressure is equal to zero:

$$P_{in} = P_{out},$$

which means that the balloon is not swollen, but very flexible and may even be wrinkled and therefore cannot harm the adjacent body tissue.

It shall be mentioned that all equations above are true independent of the filling medium, for a fluid like water as well as for air or another gas.

An inverted balloon structure made from silicon elastic polymer, for a short-term trans-abdominal access has been described by Williamson in U.S. Pat. No. 5,545,179. The device is designed to provide a gastight passageway for the insertion of surgical instruments against an inflated gas filling inside the abdominal cavity. The compliant balloon element is therefore distended elastically to its working state configuration. The required filling pressure for distending the balloon and the solid pressurized consistency of the resulting sealing structure does not allow for an atraumatic placement over prolonged periods of time, and is therefore removed after the procedure.

The present invention is explicitly designed to put the smallest pressure load on the tissue. The required seal pressure is reduced to and below the level of tissue perfusion pressures, whereby the sealing toroid is shaped to or beyond the maximum diameter of the intestinal organ, evading any stretch of the balloon wall, basically effecting the seal against secretions and fecal material as a flaccid, tensionless body, able to follow body movements and changes of organ cross-section and shape. The balloon is made from a thin-walled material of low compliance, granting only restricted elastic deformation of the pre-shaped balloon geometry, when being exposed to a force from the outside or the inside of the body.

While Williamson describes a gas-sealing device, the invention highlights the continuous release of bowel gas as a decisive feature of the closure system. Defined passageways, shaping within the compressed inner access channel during inflation, allow for a seal against liquid and solid materials, yet enable gas to escape from the bowel.

In case of the embodiment of the inverted balloon structure as a seal for an artificial intestinal opening, the device shows an intra-intestinal, a trans-abdominal, and an outer cap portion. The intra-intestinal part is primarily functioning as a anchoring and seal element, resting on the abdominal fascia and securing the device from being expelled. The trans-abdominal segment preferably has a slim, narrow configuration, allowing it to pass through the abdominal opening, largely minimizing the contact to the surrounding anatomical structures. The outer cap element is primarily designed to protect the outer portion of the stoma against drying out and mechanical irritation.

The inverted balloon structure, in case of its embodiment as an anal seal device, is made of an intra-rectal and a trans-anal portion. The intra-rectal part is primarily functioning as a anchoring and seal element, resting on the rectal floor. The trans-anal segment can be designed sufficiently large in diameter to unfold against the anal channel without distension of its wall in this segment, or in slim narrow fashion, that it minimizes the contact to the anus. Further, the device has a pre-anal portion, functioning as a bolster, securing the device in its trans-anal position.

The balloon is fabricated preformed to or beyond its working state dimensions and therefore needs not to be distended by a high, potentially perfusion impairing filling pressure. In order to reach the desired anchoring and closure performance of the balloon, the required balloon filling pressure can be kept equal or close, with only a few millibars of overpressure $p_{excess}$, for example $p_{excess}<50$ mbar, preferably $p_{excess}<20$ mbar, especially $p_{excess}<10$ mbar, more special $p_{excess}<5$ mbar, to the physiologically acting pressure inside the rectum or the respective organ or body cavity.

By pre-shaping the balloon to measures, sufficiently exceeding the dimensions of the exposed anatomical cavity or space, the described low-pressure performance of the device can be further optimized. The oversized thin-walled and membrane like balloon wall is then shaping multiple reserve folds, folding in the surplus balloon material. Since the intestinal lumen can thus be occluded and sealed without any force intensive distension of the balloon wall, the pressure, which is exerted on the intestinal mucosa and the anal tissue corresponds closely to the filling pressure of the balloon. The user can therefore determine the effective trans-mural force on the balloon exposed tissues barometrically, via a filling port that is reaching to the outside of the body.

Since the balloon is not in a distended and stretched, but largely flaccid or infolded state, it can adopt itself to natural conditions, for example can follow an abrupt bend in the intestine or adjust to dynamic changes of the shape of the space of the surrounding cavity or organ.

It is of great importance that the balloon does not comprise nor integrate a shaft element of limited flexibility, projecting into the intestine. The intra-intestinal (intra-rectal) and trans-abdominal (trans-anal) sections of the device are made from a single inverted, thin-foil balloon body and are therefore highly flexible, adjusting snugly to the morphology of the anatomical structure; they are inserted in.

Both ends of the balloon are situated on one and the same side of the torus (due to the inversion of the balloon ends), specifically on the side facing away from the interior of the person's body. There, the balloon ends are fastened to one or more sleeve elements, which are preferably situated outside the body of a person.

The unfolded toroidal balloon inside the bowel or the rectum has room to deploy, thereby developing an anchoring function. The neck region, made by the inverted balloon ends, is tapered with respect to the toroidal balloon per se and extends, for example, through the anal channel or the abdominal wall. It consists of two concentric layers of thin-walled tubing, making the neck a flexible and readily collapsible structure. Since one balloon end is narrower than the other, there remains an annular gap between the coaxially inverted ends, which is in open connection to the toroidal interior of the balloon.

The open central lumen of the inverted balloon structure, which does not communicate with the interior of the balloon, serves as a connecting pathway from the body inside to the outside. It is advantageous in this regard that the central lumen is pressed flat by the pressure inside the torus, sealing against the free passage of solid and semi-solid bowel contents through the central channel. The collapsed inner tube end forms circular eyelet-like openings at its outer lateral ends, allowing for gaseous media to escape from the body inside to the outside continuously.

The formation of gas-releasing eyelets, reaching axially from the distal to the proximal end of the collapsed inner tube, is essential for the long-term placement of an intestinal seal, as without a sufficient release, the bowel gases accumulate and painfully flatulate the patient.

The cross-sectional areas of the forming eyelets are largely determined by the thickness and elastic properties of the material forming the inner concentric tube end. The appropriate composition of material thickness and pliability in conjunction with a preferred balloon filling pressure range will be described herein below.

The formation of gas release efficient annular channels within the collapsed central lumen can be modified by additional tube foil segments or material layers, put on permanently or inserted removably into the inner tube end of the coaxial tube end arrangement.

Such a reinforcement of the inner tube layer can increase the cross-sectional area of the eyelets forming in the collapsed state of the inner tube, thus enhancing the gas release performance. Further, the reinforcement can stiffen the deflated balloon to a degree that facilitates the insertion of the intra-intestinal (intra-rectal) device portion into the stoma.

In case of a removable, stiffening tube-foil element, the gas release effect can be increased by positioning the reinforcing tube foil inside the open lumen. The element can be equipped with a filter component at its proximal end, which locks the reinforcing tube inside the cap structure.

Especially in irrigating patients, the removable element can be useful. Before the irrigation is performed, the reinforcing tube foil is pulled. Then an irrigation hose can be connected to the proximal opening of the central access lumen of the reversed balloon. After instillation of the irrigation fluid, and the infusing hose is disconnected, the collapsed access lumen seals then efficiently against fluid and enables the patient to move freely, till the bowel activity sets in and the closure system can be removed.

The inverted balloon is made of a thin-walled, soft and pliable polymer. It is prefabricated as to its outer dimensions in the working state inside the body, or beyond that, having a significantly residual dimension.

Preferably, the balloon is inflated only in order to deploy the balloon envelope. The balloon material allows the balloon to stretch to only a small extent, since it is largely inelastic. The balloon therefore does not de-shape elastically when being exposed to an external force and therefore can't slip out of the body orifice in which it is inserted. On the basis of higher material hardness, in the range of, e.g., Shore 80 A to 60 D, the balloon structure can be manufactured to very thin thickness in the range of 10 to 50 µm, preferably 10 to 25 µm, giving the balloon the required mechanical performance of a balloon membrane. Though being fabricated to very low thickness, the high material hardness restricts the compliance properties, and grants the stability of the preshape.

The polymer used for the making of the balloon is preferably polyurethane (PUR) as, e.g., Pellethane 2363 from Dow Chemical or, e.g., comparable polymers from the Elastollan LP 9291 family from BASF. Further, polyurethane/polyvinyl fluoride blends, or other materials with comparable elasto-mechanical properties to the above named polyurethane families can be used. On the other hand, it is preferred that polyurethane shall be the main component in such blend, and such blend shall not comprise any silicone elastomer or elastomer with silicon typical compliance properties. Besides polyurethane (PUR), low-density polyethylene can be used, as well as ethylene vinyl acetate (EVA), polvinyl acetate (PVC) and PVC/EVA blends.

The preferable way of manufacturing of such thin-walled material is a hot-mold blowing technique, whereby pre-extruded balloon material is stretched and the stretched balloon material is then blown by pressure, which is applied in the inside of the raw tube, into a heated mold cavity, and afterwards chilled down. The applied stretch orientates the amorphic portion of the (PUR) polymer, granting very durable, mechanically strong balloon structures of very low wall-thickness.

In one embodiment, the inverted balloon is provided with a connecting hose port that is joined to a plug. Once the plug has been inserted into the abdominal wall, the balloon is deployed through a channel located in the plug and comes into contact by its outer wall with the intestinal wall. To facilitate the insertion of the inverted balloon through the abdominal wall into the intestine, the plug is provided with a cavity in which the collapsed balloon can be housed. The plug itself is preferably form-lockingly connected to a sealing cap that is known per se, which can be affixed to the abdominal wall by an adhesive substance after the plug is inserted into the abdominal wall.

The preferred embodiment of the inventive subject matter, however, provides that the plug comprise two sleeves able to be fitted one inside the other and that the balloon have two connecting hose ports whose mouths are each connected to a is respective one of the sleeves. It is favourable in this case if one mouth has a diameter adapted to the outer sleeve and the other mouth a diameter adapted to the inner sleeve. Both mouths can be glued to the sleeve walls. The mouth joined to the outer sleeve is then fastened to the outer wall of the sleeve, whereas the mouth joined to the inner sleeve is glued to the inner wall of the inner sleeve.

To form the cavity on the plug, the inner sleeve is implemented as shorter than the outer sleeve, so that the cavity present in this region suffices to house the collapsed balloon.

In further development, the inner sleeve can be provided in its interior with a filter element, allowing gases to be released, but preventing the outflow of liquid material.

This closing system configured in this manner produces a good seal that keeps fluid secretions and fecal material from escaping to the outside. Moreover, collection bags, or the like, are rendered superfluous.

To remove the stool, the closure device can be deflated and removed completely from the body opening. In case of a plug, comprising two connectable sleeve elements, as described above, the inner sleeve can be withdrawn from the outer sleeve in a very simple manner and the balloon itself can be pulled through the opening in the outer sleeve. If the balloon is suitably dimensioned, it can serve as the collecting recipient for the stool.

For cases in which the size of the balloon is not adequate for this purpose, a special, larger collection receptacle for the stool can be used, which can be connected to the sealing cap by a first adapter and to the inner sleeve by a second adapter. Via the second adapter, the inner sleeve, which is inserted force-lockingly into the outer sleeve, can be withdrawn from the latter. It takes the balloon along with it in the process, and also withdraws the outer sleeve from the sealing cap once the balloon has been pulled all the way through. The stool can then be emptied completely into the collection receptacle.

BRIEF DESCRIPTION OF THE DRAWINGS

Further features, characteristics, advantages and effects based on the present invention will be apparent from the following description of several preferred exemplary embodiments of the invention and from the drawings.

In the drawings:

FIG. 4 shows the closing system with the inner sleeve and the balloon withdrawn.

DESCRIPTION OF THE PREFERRED EMBODIMENTS

Figure 1A:
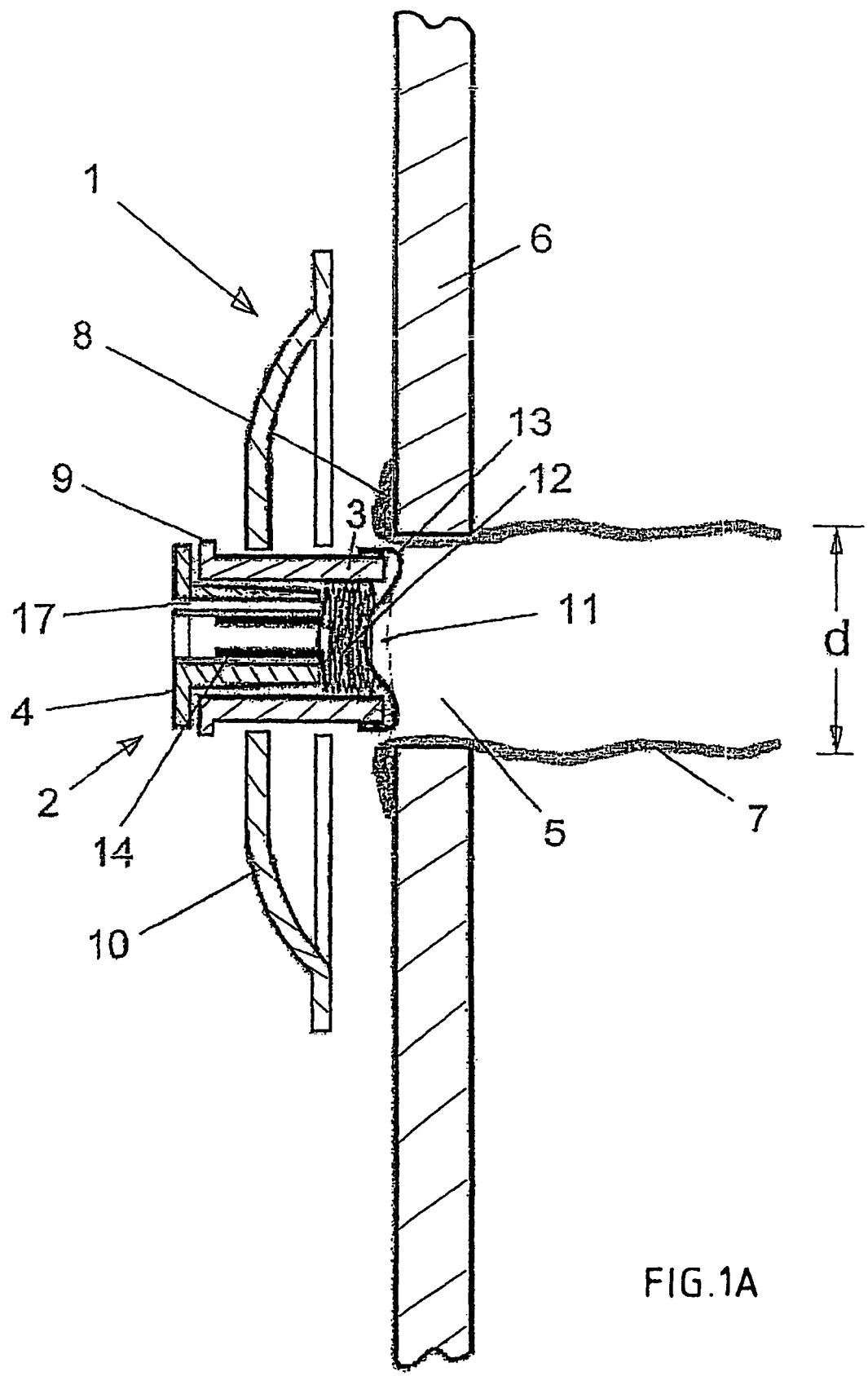
FIG. 1A is a section through an abdominal wall and a surgical stoma therein, with the closing system in longitudinal section during the process of insertion into the stoma, whereby in the insertion state of the device, the balloon is packed inside a plug-like housing.

Represented schematically in FIG. 1A is the closing system 1 for use with a colostomy, specifically based on an embodiment in which a plug 2 is composed of sleeves 3 and 4 that can be fitted one inside the other. Inner sleeve 4 is in adjacent contact inserted into outer sleeve 3. To this end, it is configured as slightly conical.

In the figure, the closing system 1 is shown being inserted into an opening 5 in the abdominal wall. An abdominal wall 6 is of normal configuration. A bowel 7 is sutured by its end 8 to the abdominal wall 6 in a manner that is known per se.

With its externally disposed flange 9, outer sleeve 3 grasps a sealing cap 10, which, when the plug 2 is inserted, completely comes into contact with the abdominal wall and can be glued thereto. It should be noted that the sealing cap 10 provides extra security for the patient in regard to the escape of body fluid. In addition, the cap protects the short segment of bowel exteriorized to the surface of the body. This segment is otherwise left unprotected against mechanical irritations. In particular, however, the sealing cap helps to prevent the drying and ulceration which at this location threatens the exteriorized bowel segment. It is also sufficient per se if plug 2 or outer sleeve 3 is provided for this purpose with an enlarged annular flange 9 that covers the edge of the opening 5 and the exteriorized segment of bowel. In cases of preserved innervation of the terminal segment of bowel, a cap element is not necessarily required, since the propulsive movements of the bowel constantly strive to push the obturating balloon toward the outside of the body, against the inner abdominal wall.

Inner sleeve 4 may be configured as shortened compared to outer sleeve 3, thereby producing a cavity 11 into which a collapsed balloon 12 can be folded. As shown in FIG. 1A, the balloon 12 has two connection ports 13 and 14 by which it is connected to outer and inner sleeves 3,4 respectively.

Balloon 12 with connection ports 13 and 14 is made of a thin-walled, inflatable polymer and has when inflated a diameter D that is appreciably greater than the diameter d of the bowel segment concerned. Diameter D is produced in various sizes and can in this way be adapted to the size of bowel diameter d. This also applies to the execution of the plug 2 and the sleeves 3,4, which in this embodiment of the invention are inserted into the trans-abdominal bowel access. In the exemplary embodiment according to FIG. 1A, the larger connection port 13 is pulled by its mouth 15 into the outer wall of sleeve 3. The mouth 16 of connection port 14 is fastened to the inner wall of inner sleeve 4. The fastening can be done with glue, but clamping rings, or the like, are also feasible. For the operation of inflating the balloon 12, which by virtue of its being fastened to plug 2 is configured as double-walled, channel 17 is provided in inner sleeve 4.

Sleeve 3 is preferably made from a material of softer hardness than the inner sleeve 4, thereby reducing the irritating effect of a solid structure, which is continuously placed inside the bowel opening.

Figure 1B:
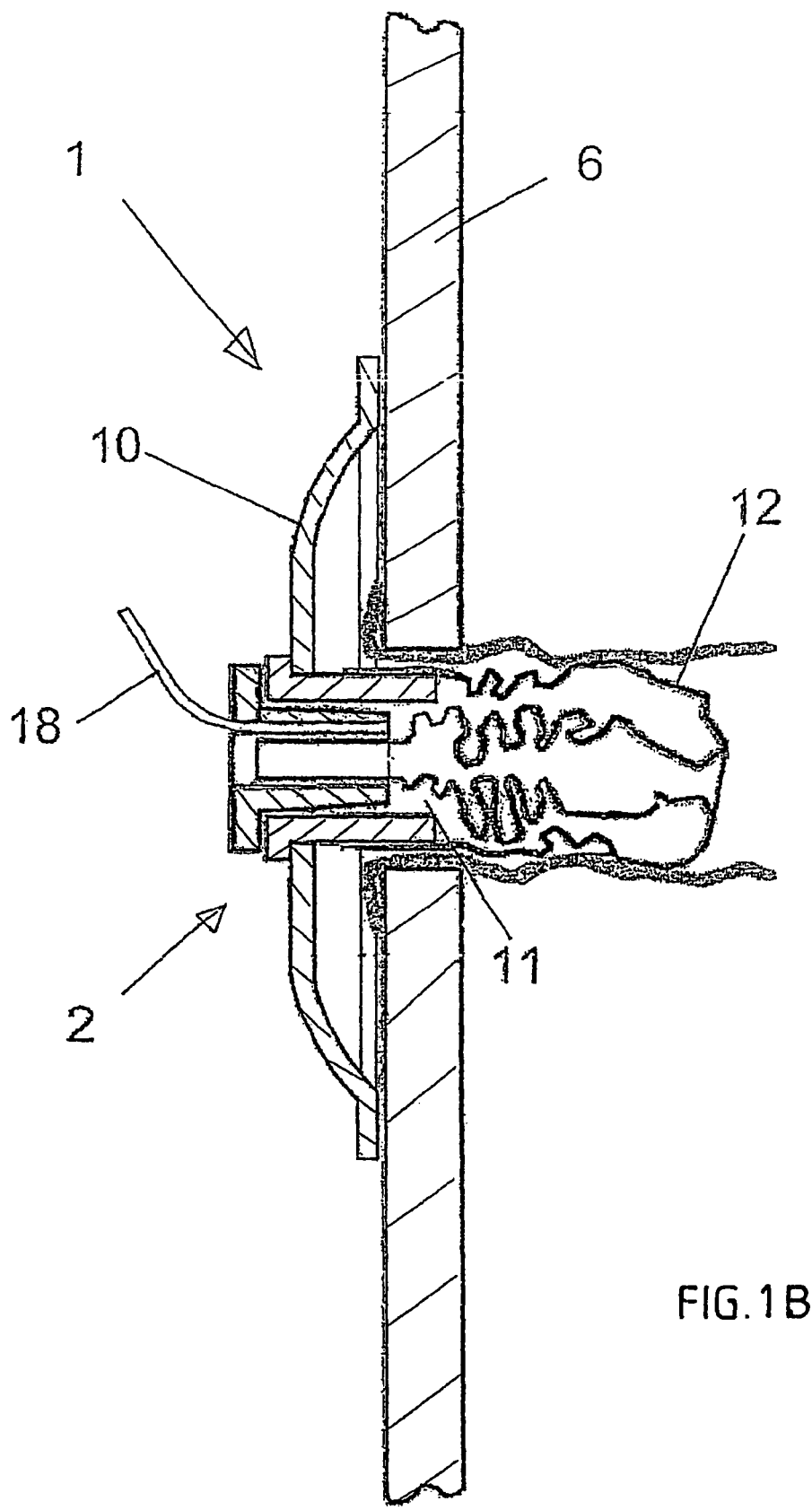
FIG. 1B shows the inserted closing system in section at the beginning of the process of deploying the balloon, whereby the plug-like housing reaches into the stoma orifice.

In FIG. 1B, plug 2 is fully inserted into the bowel opening, so that sealing cap 10 rests against the abdominal wall. Through a hose nipple 18, air is pressed into the balloon 12 so that the balloon deploys. In the figure, the beginning of the deployment is particularized. The balloon is already pushed partway out of the cavity 11 and unfolds inside the bowel lumen.

Figure 2A:
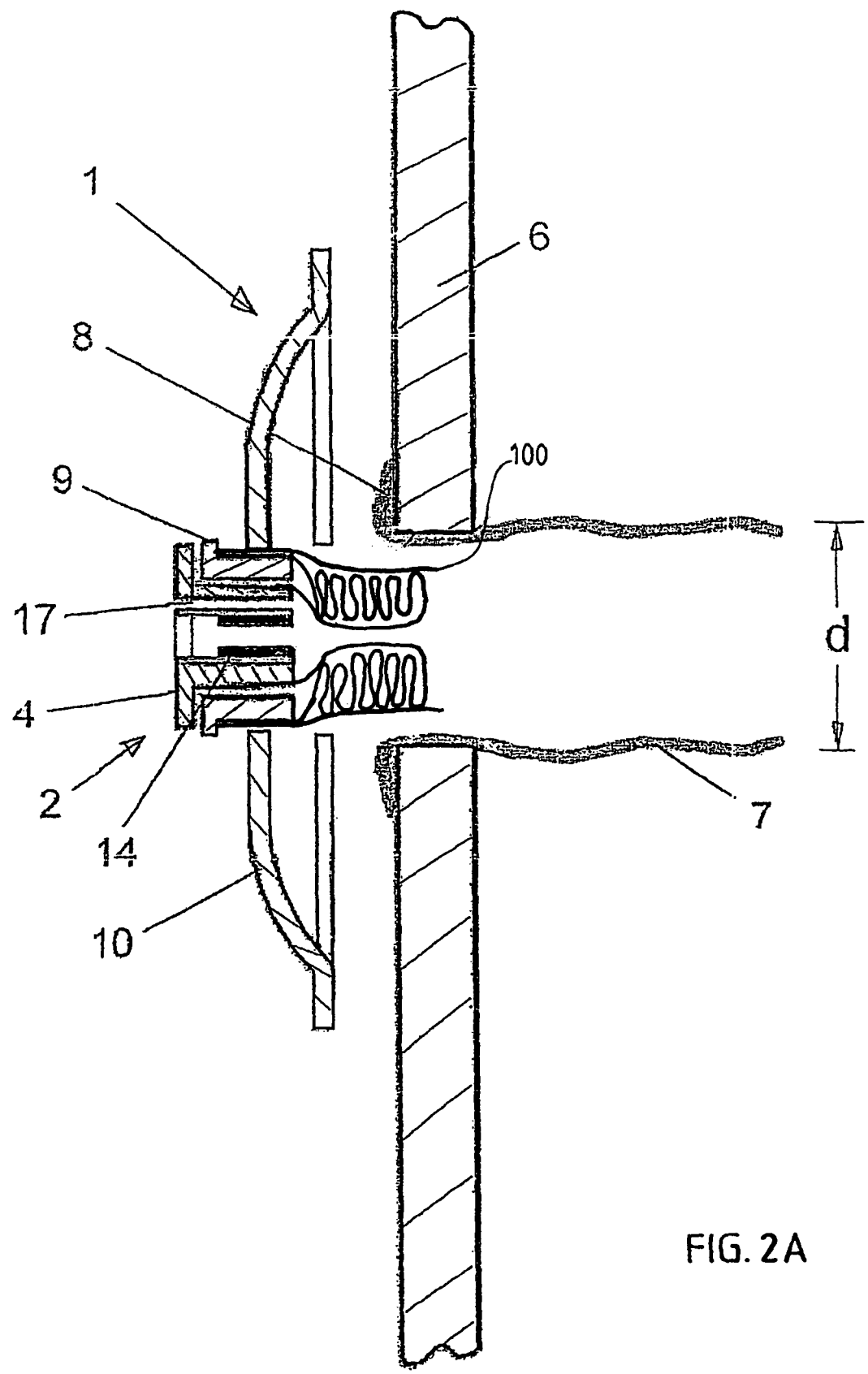
FIG. 2A is a section through an abdominal wall with the closing system in longitudinal section during the process of implantation in the opening in the abdominal wall, whereby in the insertion state of the device, the inserted balloon is packed inside a thin walled tube element.

FIG. 2A shows a similar embodiment, whereby the deflated balloon is packed inside a thin-walled, tube foil-like hose-element 100. While in FIG. 1A a plug structure of solid consistency is inserted in the opening of the body wall and resting there, in this embodiment the folded and deflated balloon is packed inside a tube foil element. Packed inside that surrounding element 100, the balloon is inserted into the orifice. Plug 2 in this embodiment is accordingly shortened to stay within the level of the cap element, not entering the orifice, when the cap is being fixed on the body.

Figure 2B:
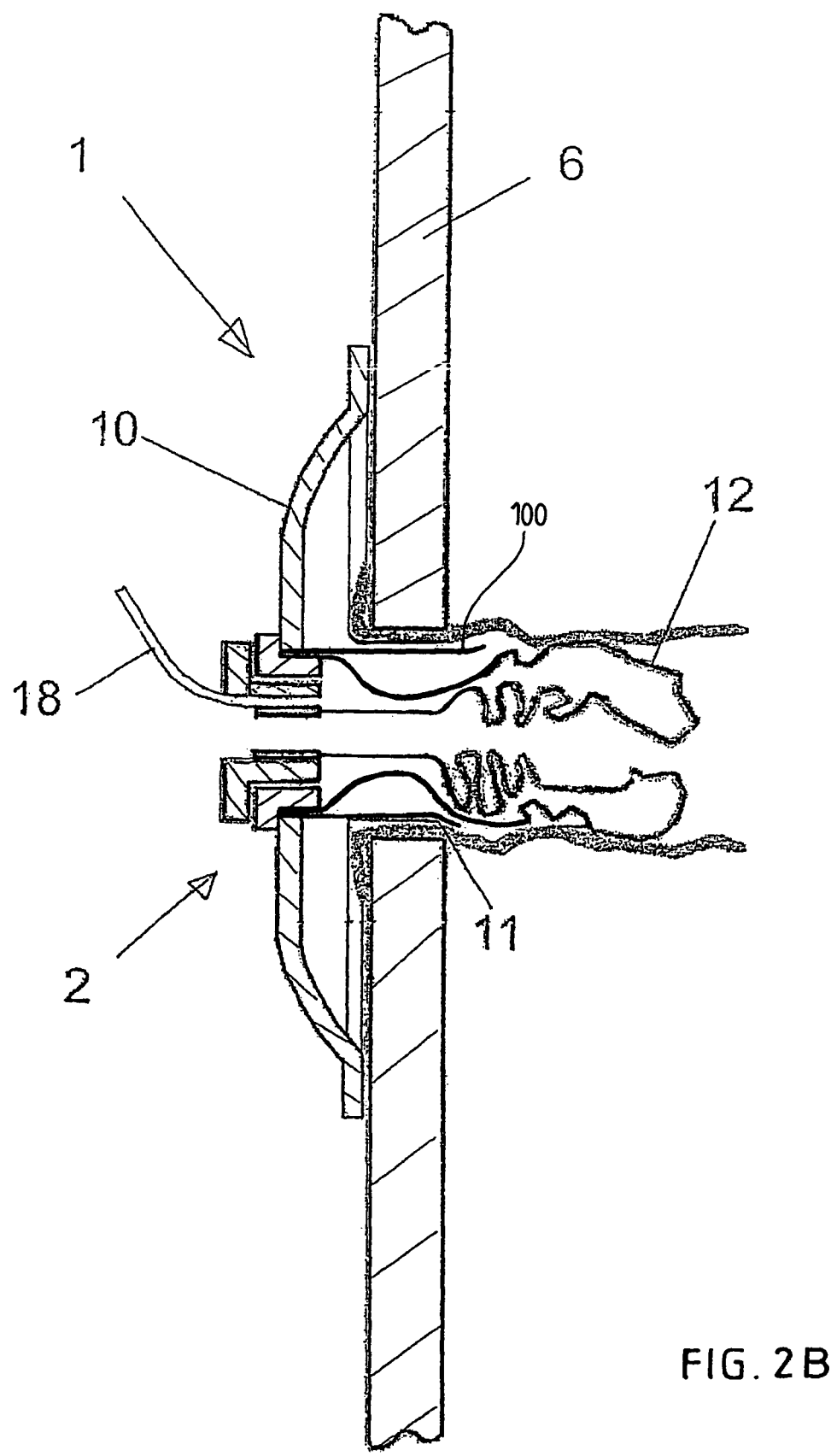
FIG. 2B shows the implanted closing system in section at the beginning of the process of deploying the balloon, whereby instead of a guiding rigid capsular element, an atraumatic tube-foil element is resting in the trans-abdominal orifice.

FIG. 2B shows how the embodiment of FIG. 2A unfolds out of the sheathing tube foil-like element 100 and deploys into the bowel space. Once the balloon has left the sheath and is developing into the bowel lumen the sheathing tube foil element remains inside the trans-abdominal channel as a soft and pliable, atraumatic foil layer.

Figure 2C:
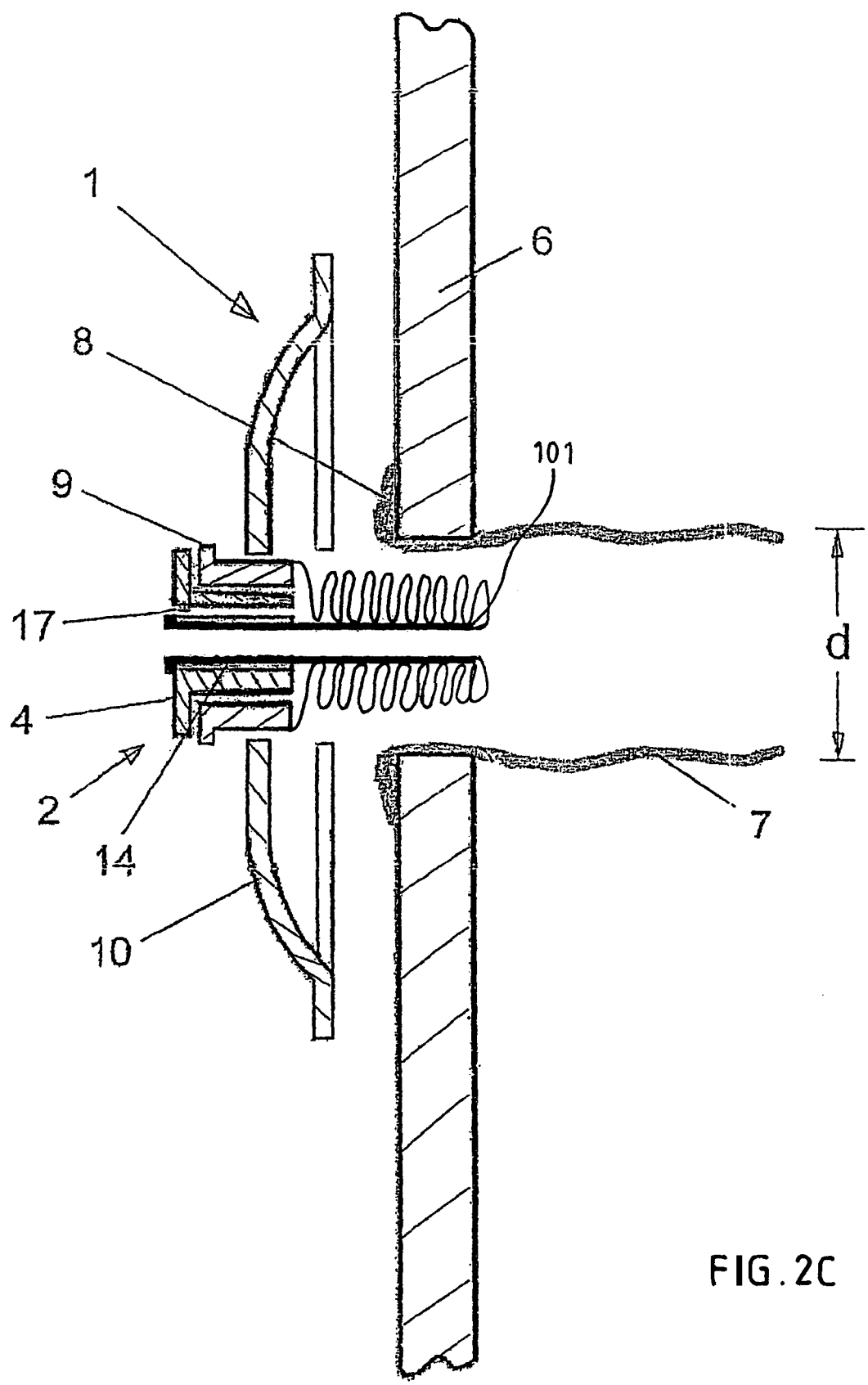
FIG. 2C shows the implanted closing system in section at the beginning of the process of deploying the balloon, whereby instead of a surrounding outer element, the balloon is packed in, the balloon is evacuated around a reinforced inner tube end, which is shaping the access channel in the centre of the everted structure.

FIG. 2C shows another embodiment of the invention, whereby the deflated balloon is not packed inside a guiding plug or sheath, but is snugly evacuated against the inner tube end 101, which preferably has a higher wall-thickness than the other portions of the balloon structure. The inner tube end 101 can be modified in its elasticity by additional reinforcing tube foil elements, which are connected to the inner tube end permanently or can be removed from the outside.

Figure 3A:
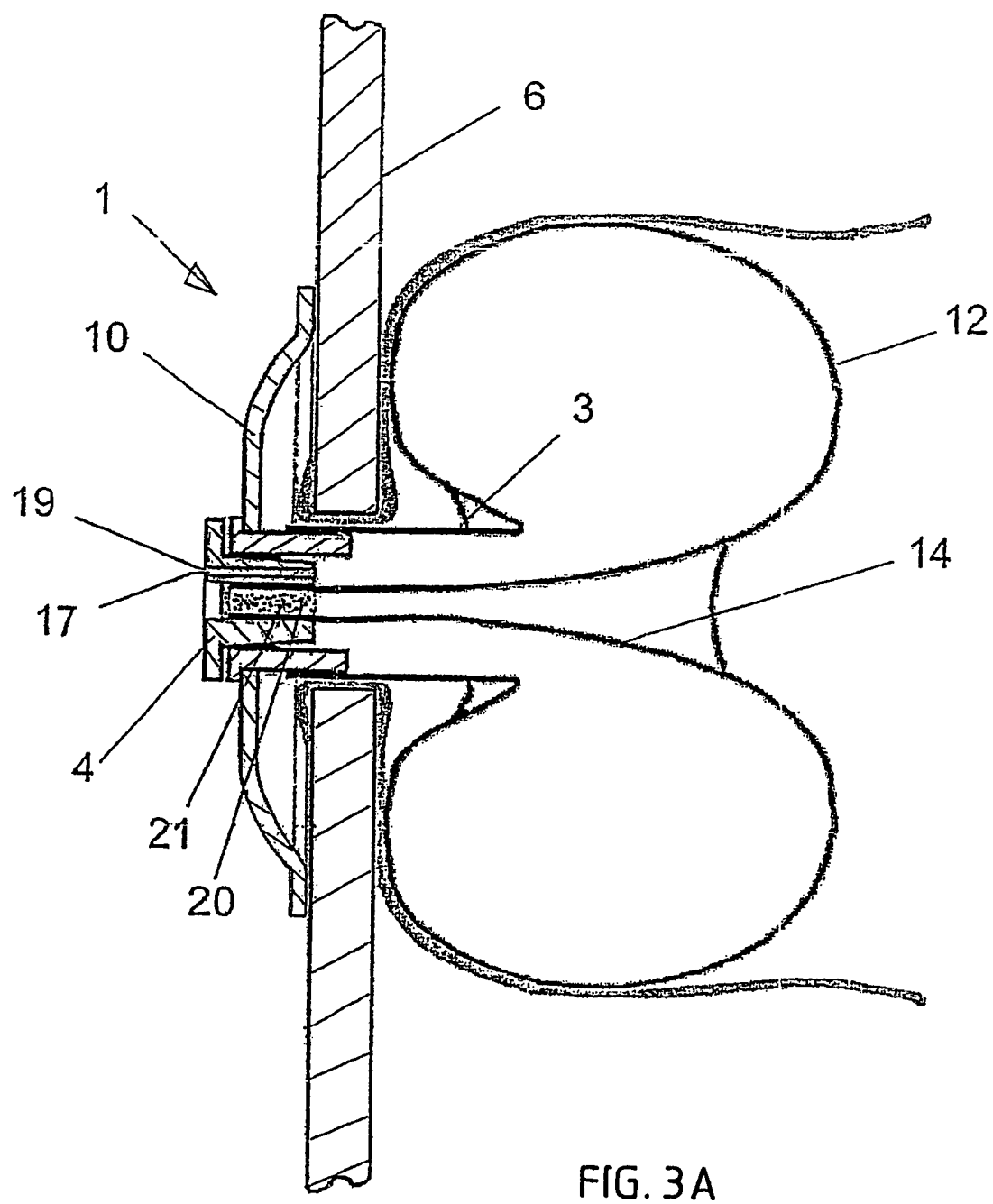
FIG. 3A shows the closing system with the balloon inflated.

FIG. 3A shows the fully inflated balloon 12, which has assumed the shape of an annular ring and rests sealingly against the wall of the bowel 7. The preforming of the balloon 12 during manufacture reflects its shape when inflated. The annular ring can be of different lengths, so that it can also be configured cylindrical and occupies a longer segment in the bowel 7. Preferably, the annular ring is configured disk shape, with an axial length of the ring of about 2 to 5 cm.

The deployed balloon 12 is configured with respect to its diameter D such that it is has the diameter or has one that is larger than the maximally distended bowel, so that in the normal resting state of the bowel, the excess balloon wall material of the outer hose, when inflated, lies in folds, which due to the very small wall thickness fold "eyelets" of roughly the size of capillaries. Fluids are largely retained in the fold eyelets and therefore can not pass the infoldings in free flow.

In the presence of such infolded balloon material, the pressure measured externally via the channel 17 corresponds to the pressure, which is exerted on the intestinal mucosa. The resulting force on the intestinal wall 7 can therefore be adjusted by the patient with a manometer, securing an applied filling pressure in an atraumatic pressure range. A factor that is favourable for sealing is that the annular ring also bows outward toward the abdominal wall 6 and there presses sealingly against the bowel 7 on the inside of the abdominal wall 6.

Preferably the diameter D of the preshaped balloon exceeds the maximum diameter of the bowel by 10 to 50%, preferably 10 to 15%.

The portion of the device, which is positioned inside the abdominal wall, connecting the annular ring structure with the extracorporeal cap element, preferably has a diameter smaller than the lumen of the trans-abdominal opening.

Installed in the air channel 17 of inner sleeve 4 can be a check valve 19 that keeps the air in the balloon 12. This valve can be opened if necessary and the air vented. Connection port 14 effectively forms an inner wall of the balloon 12, which constitutes an escape channel 20 for the gases produced in the bowel 7. Installed in this channel 20 or in inner sleeve 4 can be a carbon or cellulose filter 21.

Figure 3B:
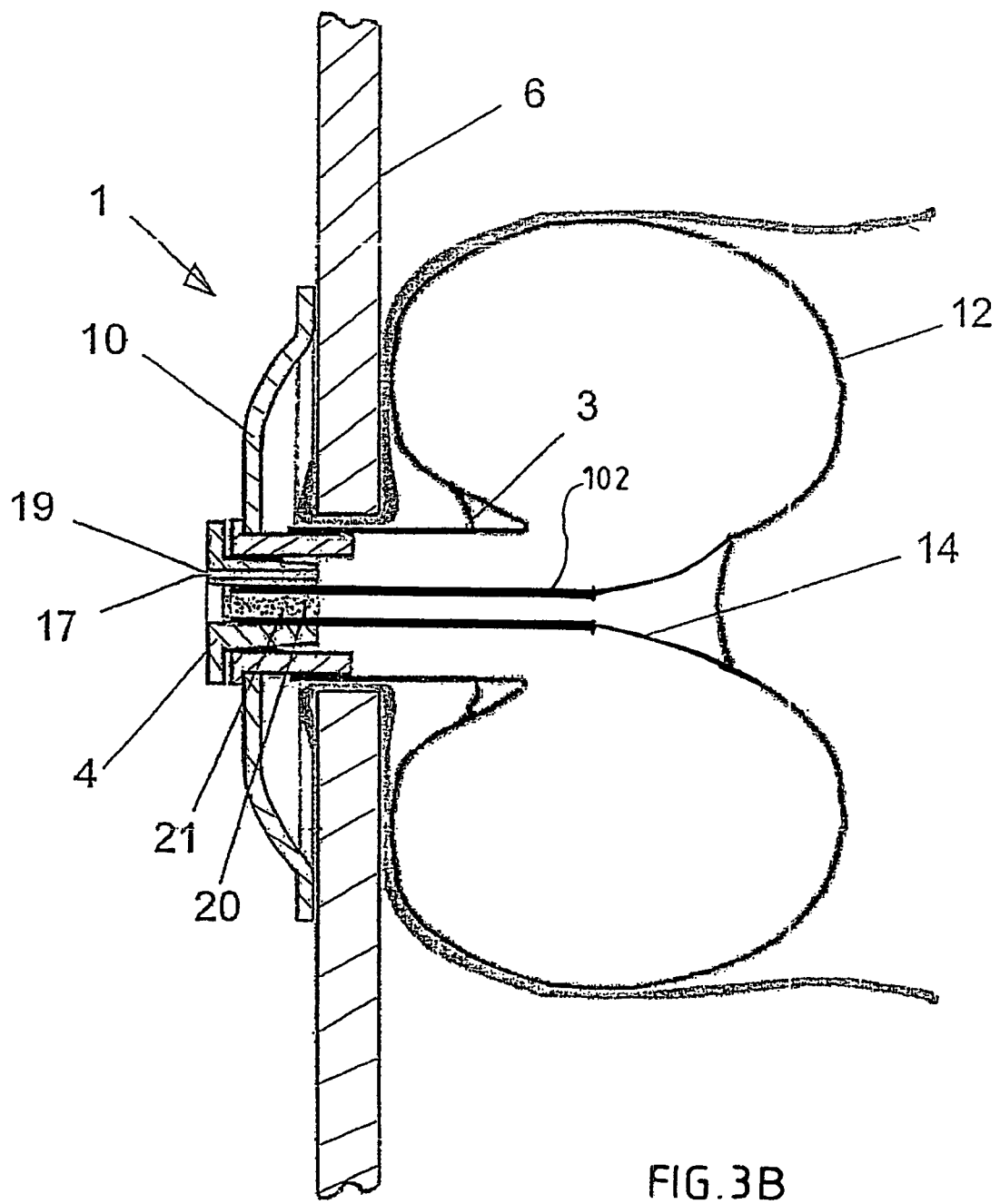
FIG. 3B shows another closing system with the balloon inflated.

In FIG. 3B, in order to increase or modify the cross-sectional diameter of the central gas-releasing eyelets, shaping within the collapsed open channel 17, an additional tube foil element 102 can be integrated into the opening. The gas-releasing foil element 102 can be either permanently fixed to the channel 17 defining inner tube end or can be designed as an element, which is removable from channel 17. It is preferably made as a soft and pliable foil-tube like structure, whereby the shaping gas releasing eyelets in the inflated collapsed state can be varied and defined by material thickness and elasticity of the tube element.

To evacuate the bowel, it is possible in many cases to let the air out of the balloon 12 or open valve 19, or withdraw inner sleeve 4 from outer sleeve 3. Withdrawing the inner from the outer sleeve causes the obturating balloon to lose pressure and thus deflate. The entire balloon 12 can then be pulled through the inside of outer sleeve 3. The then externally disposed balloon 12 can receive the stool. After cap 10 with outer sleeve 3 has been detached from the abdominal wall 6, the stool can be removed easily and safely.

FIG. 4 shows the position of the balloon 12 in which it has been pulled through outer sleeve 3 and is ready to receive the stool.

Figure 5:
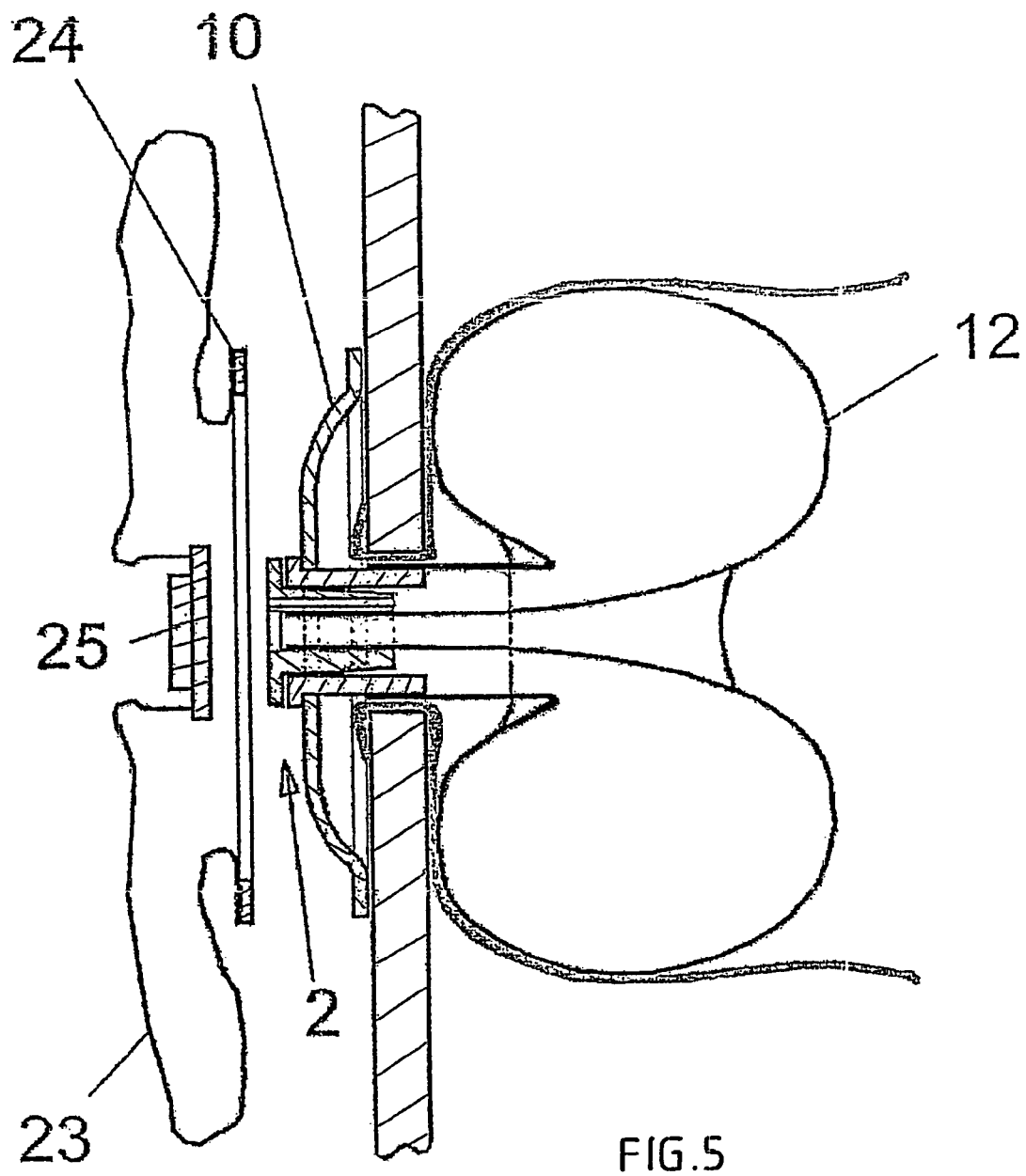
FIG. 5 shows the closing system with a collection receptacle ready to be fitted thereto.
Figure 6:
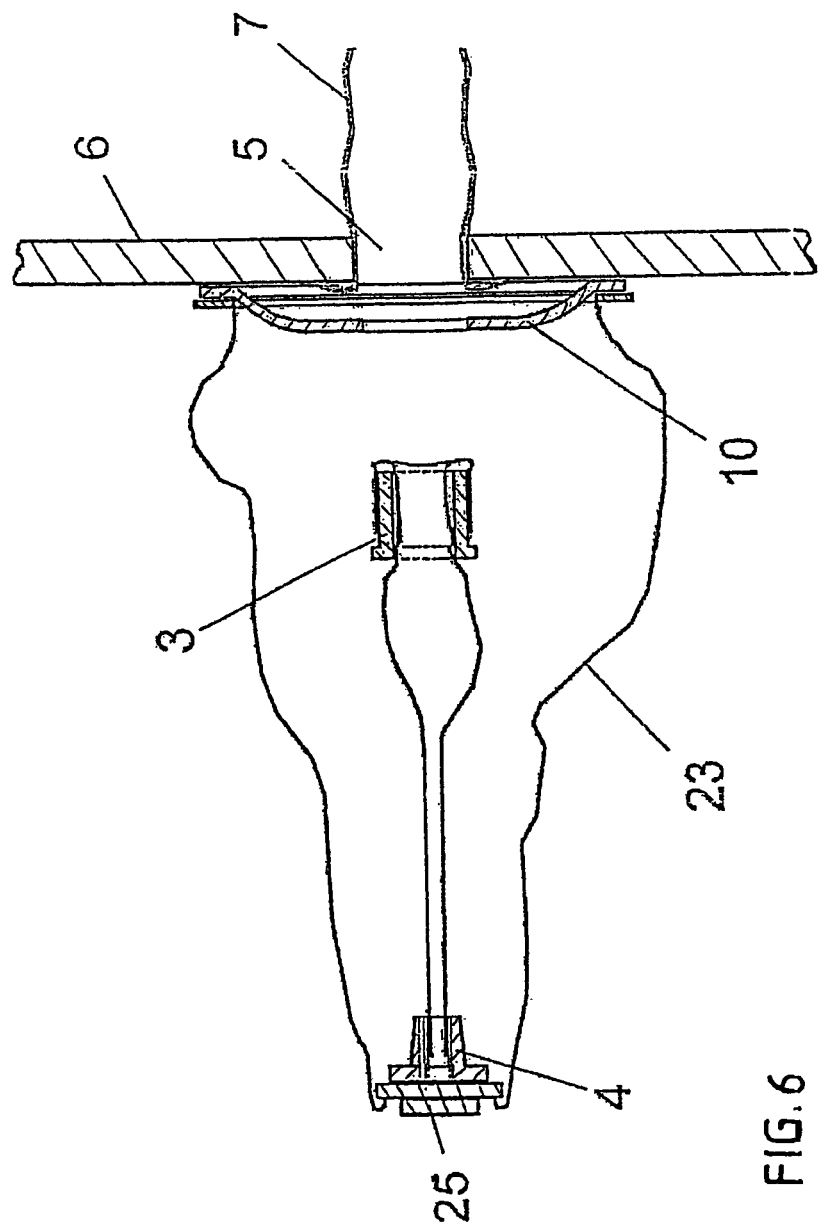
FIG. 6 shows the closing system with the inner sleeve withdrawn, including the balloon, and with the collection receptacle intended to receive the stool.

Since the balloon 12 will not be adequate to receive relatively large amounts of stool in every case, it is possible to configure the plug 2 and/or the sealing cap 10 such that an appropriately configured collection bag 23 can be fastened thereto. As shown in FIG. 5, the collection bag 23 has an annular flange 24 that can be connected to sealing cap 10 and a lid 25 that can be placed on inner sleeve 4. By the exertion of traction on lid 25, inner sleeve 4 is withdrawn from outer sleeve 3 and, as represented in FIG. 4. Balloon 12 is withdrawn through the inner opening of outer sleeve 3. This procedure is illustrated in FIG. 6, wherein outer sleeve 3 is also pulled out of opening 5 or its mounting in the cap 10, so that the stool can be emptied into the collection bag 23.

Figure 7:
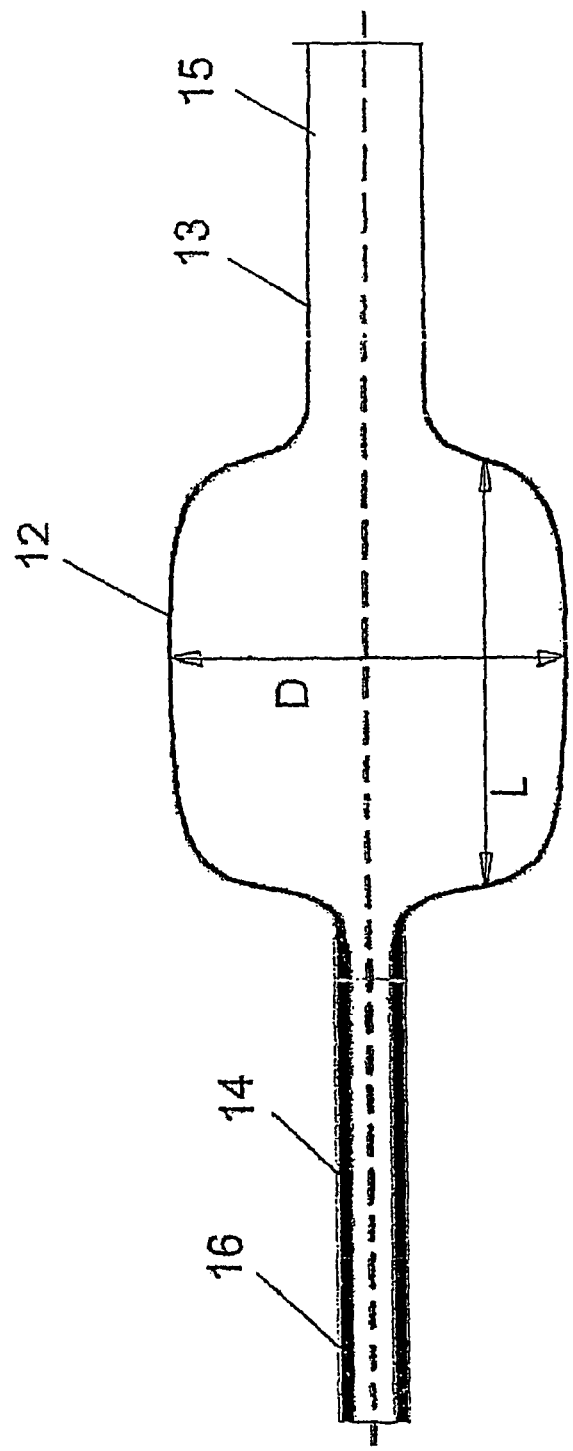
FIG. 7 is a section through the performed balloon with hose connectors, indicating the preferred embodiment with a thicker-walled, eyelet-forming central tube end.

FIG. 7 shows the preformed balloon 12 with the connection ports 13 and 14. Connection ports 13 and 14 have a relatively great length. Before they are used, i.e. connected to plug 2 or sleeves 3 and 4 of plug 2, connection ports 13 and 14 are custom-cut to an appropriate length, depending on the thickness of the abdominal wall 6. The wall-thickness of connection port 14 is preferably higher than the thickness of connection port 15, granting the formation of eyelets of sufficiently large diameter in the collapsed state of port 14 inside the body, being inflated to seal pressure.

Figure 8:
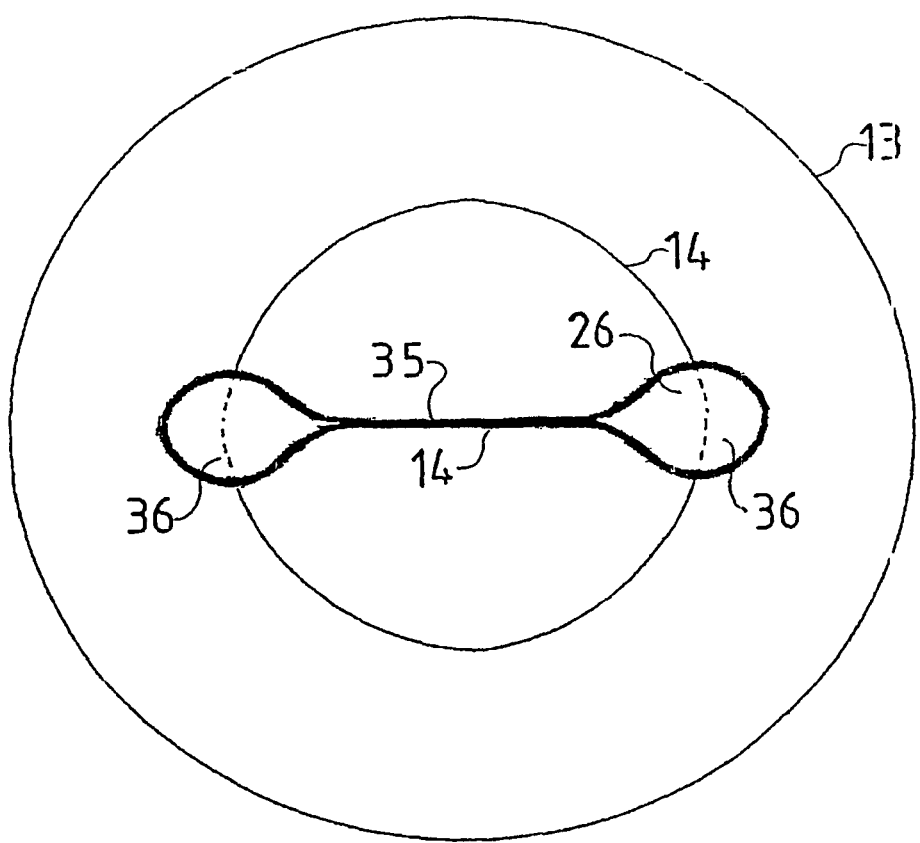
FIG. 8 is a section through the performed and inverted balloon with hose connectors.

As shown in FIG. 8, the balloon volume 28 also presses against a central lumen 26 and in so doing collapses inner hose segment connection port 14, as indicated by the thick line. The central lumen 26 is thereby largely sealed, keeping solid and semisolid material reliably inside the bowel. Nevertheless, due to the limited deformability of the thicker hose material on the inner hose segment 14, capillary-shaped passages 36 do remain on both sides of a double-ply region 35 and permit the continuous escape of gases.

With an acting balloon filling pressure of 20 mbar, the smallest diameter of a shaping eyelet or capillary-shaped passage 36 within the compressed central channel is in the range of 0.3 to 2.0 mm, preferably 0.5 to 1.5 mm.

In case of a reinforcement of the inner channel forming inner connecting port 14 by a permanent or removable structure, the diameter of the shaping eyelet or capillary-shaped passage 36 within the compressed and collapsed reinforcing element is in the range of 0.5 to 2.5 mm, preferably 0.75 to 1.5 mm.

Figure 9:
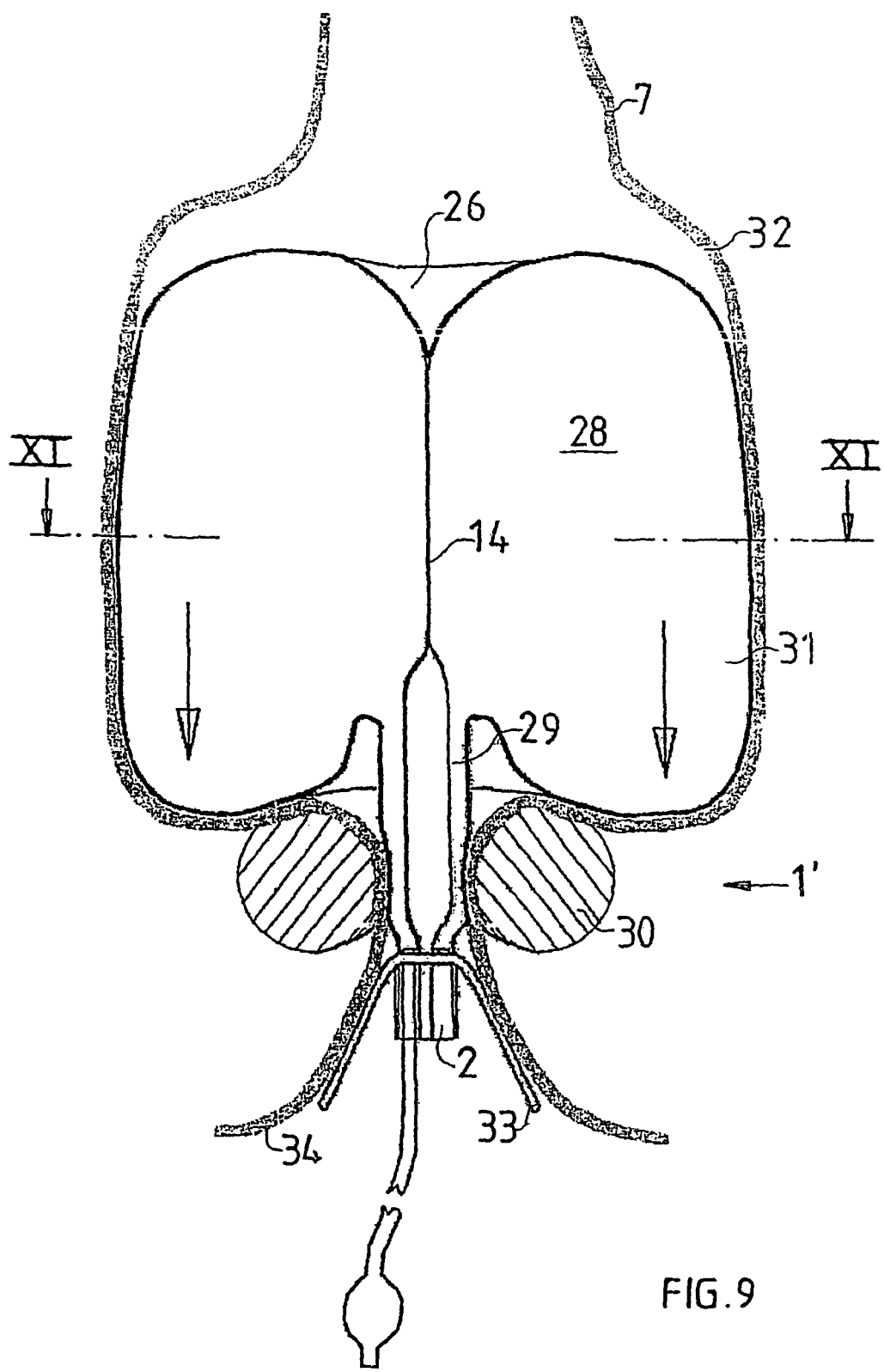
FIG. 9 is another embodiment that is suitable for use with a natural intestinal outlet.
Figure 10:
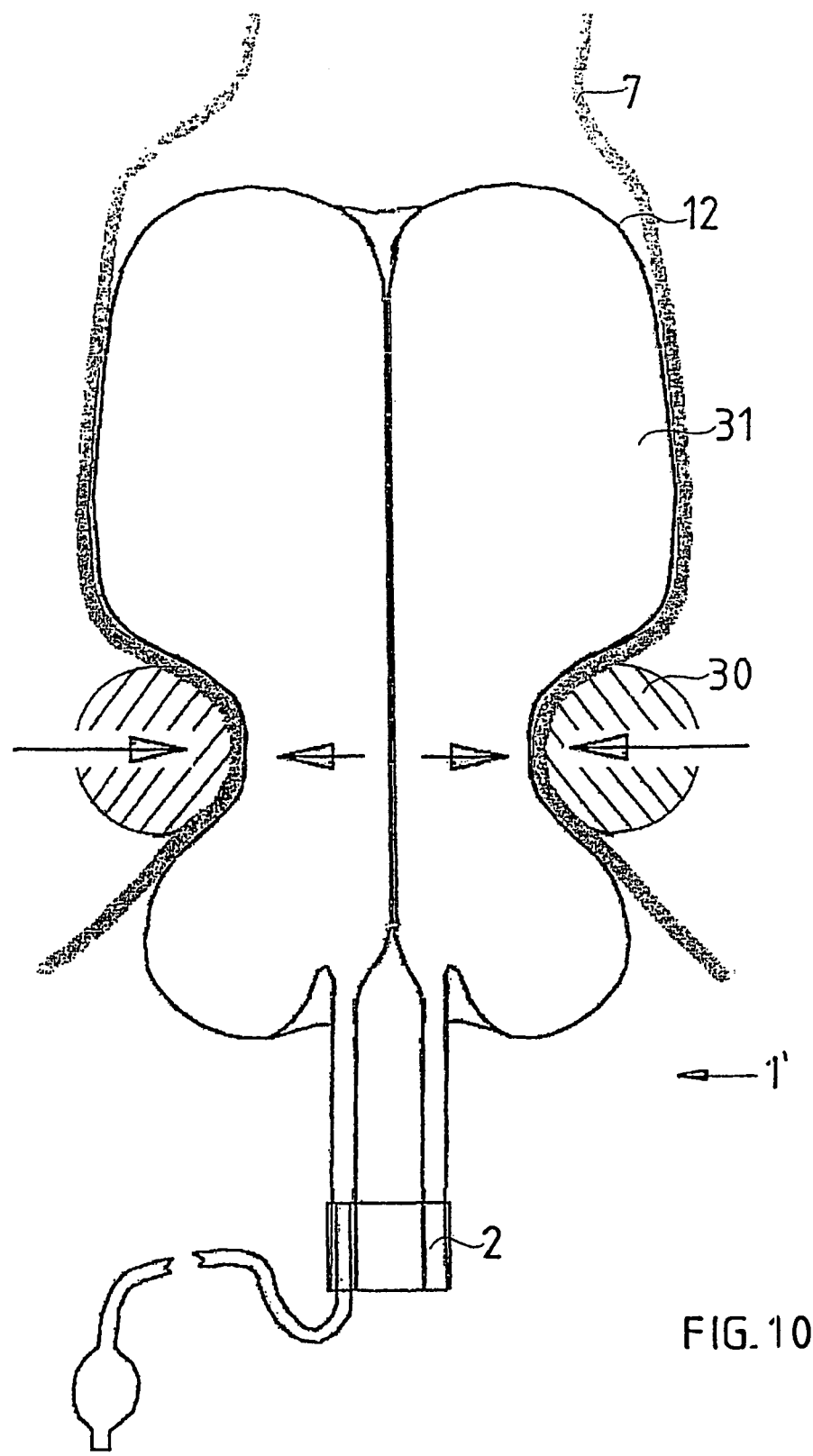
FIG. 10 shows another embodiment of the invention, optimized for use in the natural intestinal outlet.

FIGS. 9 and 10 reflect embodiments that are suitable for use with a natural intestinal outlet.

The closing system 1' used in this case differs only in detail from those described hereinabove. For example, the connection ports 13,14 can be configured as somewhat longer, thereby resulting in a pronounced neck region 29 that extends through the sphincter muscle 30 and makes it possible for an actual, radially expanded balloon portion 31 to fill the terminal rectum 32. Since when the balloon 12 is inflated its radially expanded portion 31 is pressed against the floor of the terminal rectum 32, this closing system 1' is able to anchor itself in optimum fashion. The abutment is formed in this case by a longitudinally folded sealing cap 33 that is fastened to plug 2 and whose shape is adapted to the anatomy of the anal fold 34. The sealing cap 33 can be provided with a soft fleece on the outer sides of its two wings.

Another application for the inventive closing system 1' is illustrated in FIG. 10. Here, the balloon 12 is not inserted completely into the bowel 7, but only partially, so that it is located just at the level of the sphincter muscle 30. To better guard against dislocation of the balloon 12 during normal physical movement of the patient (walking, sitting), the balloon can in the transanal segment be suitably preformed with a taper, or waisted (about 2-5 cm in diameter transanally).

To make the sealing apparatus usable for the self-care of hemorrhoidal bleeding by the patient, the body can be supplemented by an initiating and drainage element, preferably permanently fixed in the sleeve terminating segment.

The invention claimed is:

1. A closing system for a natural or an artificial intestinal outlet, comprising an inflatable balloon having an approximately toroidal structure, wherein the balloon is
   a) made from a pre-shaped thin-walled soft-foil of a polymer of low compliance,
   b) formed of a hose segment with a two-dimensional surface, which hose segment is inverted into itself, whereby two ends of the inverted hose segment extend generally coaxially with each other and are (each) connected to a respective sleeve,
   c) wherein, in the inverted, assembled and pressurized balloon, the end of an inner hose segment collapses to a flat structure, shaping channel-like bowel gas releasing passages within lateral portions thereof,
   d) and wherein said bowel gas releasing passages, at a balloon filling pressure of 20 mbar have a smallest inner diameter of 0.5 to 2.3 mm.

2. The closing system as recited in claim 1, wherein said balloon is preshaped by fabrication to a maximum inside diameter of an organ space or body cavity in which the inverted balloon structure is placed.

3. The closing system as recited in claim 1, wherein said balloon is preshaped by fabrication to a diameter which exceeds a maximum inside diameter of an organ space or a body cavity which the inverted balloon structure is placed in, by 20 to 40%.

4. The closing system as recited in claim 3, wherein said balloon is made of a thin-walled soft-foil polymer, and wherein a wall-thickness of a toroidal balloon portion ranges from 15 to 25 micrometers.

5. The closing system as recited in claim 1, wherein the polymer is a selected one of polyurethane, a polyurethane/polyvinyl chloride blend, and a comparable polyurethane-based material.

6. The closing system as recited in claim 5, wherein the polymer is a polyurethane in a Shore hardness range of 90 A to 55 D.

7. The closing system as recited in claim 1, wherein said balloon seals an intestine against fecal material and intestinal secretions at a filling pressure of said balloon of 15 to 25 mbar.

8. The closing system as recited in claim 1, wherein the end of an inner hose segment is provided with a thicker wall than other segments of said balloon structure.

9. The closing system as recited in claim 8, wherein the end is provided with a wall thickness of 30 to 50 μm.

10. The closing system as recited in claim 8, wherein said bowel gas releasing passages, at a balloon filling pressure of 20 mbar have a smallest inner diameter of 0.5 to 1.5 mm.

11. The closing system as recited in claim 8, wherein the end is reinforced by a selected one of a fixed supporting tube-foil element and an additional material layer.

12. The closing system as recited in claim 8, wherein the end is reinforced by a removable supporting tube-foil element.

13. The closing system as recited in claim 8, wherein the end, in the collapsed state, shapes said bowel gas releasing passages, at a balloon filling pressure of 20 mbar having a smallest inner diameter of 0.75 to 1.5 mm.

14. The closing system as recited in claim 1, wherein the ends of said balloon are preformed such that each of an end region of the inverted hose segment has a generally constant cross-section.

15. The closing system as recited in claim 1, wherein the inverted hose segment is preformed such that its front end, which is distal relative to the mutually coaxially ends, assumes in an inflated state a curved contour with no edge regions.

16. The closing system as recited in claim 1, wherein said balloon is preformed such that it has in an inflated state a diameter that exceeds a diameter of a bowel segment.

17. The closing system as recited in claim 1, wherein the balloon when collapsed, is housed in a cavity, provided in a plug and is directed toward the interior of the bowel.

18. The closing system as recited in claim 17, wherein said collapsed balloon is housed in a sheathing piece of thin-walled and pliable foil tubing.

19. The closing system as recited in claim 17, wherein the two ends of said balloon are each connected by their mouths to said plug.

20. The closing system as recited in claim 19, wherein said plug is composed of two sleeves fitted one inside the other and the mouth of each end is connected to a respective one of said sleeves.

21. The closing system as recited in claim 20, wherein the mouth that can be connected to an outer sleeve has a diameter adapted to said outer sleeve, and the mouth that can be connected to an inner sleeve has a diameter adapted to said inner sleeve.

22. The closing system as recited in claim 21, wherein said balloon can be pulled through said outer sleeve.

23. The closing system as recited in claim 22, wherein a filter is disposed inside said inner sleeve.

24. The closing system as recited in claim 20, wherein said plug or either sleeve is connectable to a sealing cap.

25. The closing system as recited in claim 24, wherein the sealing cap is connected in contact with said plug.

26. The closing system as recited in claim 25, wherein said sealing cap is provided with a folded structure.

27. The closing system as recited in claim 26, wherein said sealing cap and/or said plug is connectable to a collection bag.

28. The closing system as recited in claim 19, wherein either of said ends exhibits in free inflation outside the body an outer diameter of 7 to 12 mm.

29. The closing system as recited in claim 28, wherein one of said ends exhibits in free inflation outside a body an outer diameter equal to a diameter of a distal toroidal portion.

30. The closing system as recited in claim 29, wherein one of said ends exhibits in free inflation outside a body within a trans-anal segment, a preformed shape with a waist of 2 to 5 cm in diameter.

31. The closing system as recited in claim 27, wherein the collection bag is connectable to said sealing cap and to an inner sleeve.

32. The closing system as recited in claim 1, wherein the ends of the hose segment, which is inverted to form said balloon, are not in direct contact with each other.

* * * * *